United States Patent [19]

Itoh et al.

[11] Patent Number: 4,486,080
[45] Date of Patent: Dec. 4, 1984

[54] DEVICE FOR DETECTING BLINKING OF AN EYE UNDER EXAMINATION

[75] Inventors: Kiyoshi Itoh; Yukiyasu Nishikawa; Shuji Hoshika, all of Saitama; Masato Hara; Hideyuki Ishiai, both of Tokyo; Ikuzo Okamoto, Saitama; Osamu Shindow, Tokyo, all of Japan

[73] Assignee: Asahi Kogaku Kogyo Kabushiki Kaisha, Tokyo, Japan

[21] Appl. No.: 259,622

[22] Filed: May 1, 1981

[30] Foreign Application Priority Data

May 2, 1980 [JP] Japan .................. 55-59207

[51] Int. Cl.³ .................. A61B 3/14; G03B 29/00
[52] U.S. Cl. .................. 351/206; 354/62
[58] Field of Search .................. 351/7, 13; 354/62

[56] References Cited

U.S. PATENT DOCUMENTS 3,802,768  4/1974  Robinson et al. .
3,880,501  4/1975  Munnerlyn .
4,149,787  4/1979  Kobayashi .................. 351/7

Primary Examiner—Rodney B. Bovernick
Attorney, Agent, or Firm—Sughrue, Mion, Zion, Macpeak & Seas

[57] ABSTRACT

An opthalmological instrument including a blinking detecting device for positively detecting when an eye is blinking to thereby eliminate errors in optical measurements due to variations in the signal light produced by the blinking. An optical system receives light beams reflected from a portion of an eye under examination to form an image of the front portion of the eye in an image plane. An image pickup element is disposed at the image plane and produces an output video signal in response thereto. A detecting circuit which receives the video signal determines whether or not the image pickup element exceeds a predetermined threshold value. If the threshold value is not exceeded, an indication is produced that blinking has occurred.

1 Claim, 4 Drawing Figures

DEVICE FOR DETECTING BLINKING OF AN EYE UNDER EXAMINATION

BACKGROUND OF THE INVENTION

The present invention relates to a blinking detecting device which detects whether or not an eye has blinked during an eye examination with an opthalmological instrument.

During automatic measurements with an opthalmological instrument in which an optical pattern is projected onto the eye and the eye is examined using light beams reflected from the retina, the eye often blinks during which times the opthalmological instrument cannot receive light beams reflected from the retina. If the light beams reflected from the retina are intercepted by the eyelids during the examination, the interception is detected as a signal variation by the detector. Accordingly, the result which should be obtained by analyzing the true signal variation may be subject to a large error. Thus, blinking provides a large problem during these measurements.

In order to detect the blinking, a method has been disclosed in U.S. Pat. No. 3,802,768 in which an analog output signal corresponding to the variations in image formation of the above-described optical pattern is detected and an automatic eye refraction meter for analyzing the signal to calculate the eye refractive power is used to detect the variation rate of the analog signal thereby to detect the start of the blinking.

However, the conventional method is still disadvantageous in the following points. If the pupil diameter is small, the analog signal has a low level, and accordingly, it is difficult to detect the blinking. The method cannot detect the eye closure period during the blinking. If the true variation rate of the analog signal is close to the signal variation rate due to the blinking, it is difficult to distinguish them from each other.

Accordingly, an object of the present invention is to provide a blinking detecting device which can positively detect whether the eye is open or closed and which is not affected by the signal level or signal variations produced by the eye under examination.

SUMMARY OF THE INVENTION

This, as well as other objects of the invention, are met by an opthalmological instrument in which optical energy (light energy) is applied to an eye under examination and light beam reflected from the eye are analyzed to determine conditions of the eye. This instrument includes a blinking detecting device composed of an optical system for receiving light beams reflected from a front portion of the eye under examination and which forms an image of the front portion of the eye in an image plane, an image pickup element disposed at the image forming plane and detecting circuit means connected to receive an output video signal from the image pickup element for detecting whether or not the video signal exceeds a predetermined threshold value.

Preferably, the image pickup element is a television camera. In a preferred embodiment, the detecting circuit means includes a comparator to one input of which the video signal is coupled and with a reference level fed to the other input thereof. The output of the comparator is coupled in sequence to first and second memories with the memories being clocked in accordance with an output vertical blanking pulse produced by a vertical blanking pulse generator which receives the video signal as its input.

DESCRIPTION OF THE PREFERRED EMBODIMENTS

Figure 1:
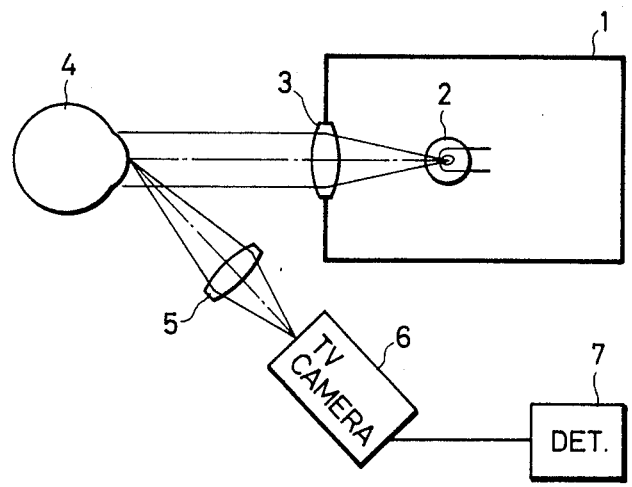
FIG. 1 is an explanatory diagram showing a preferred embodiment of a blinking detecting device of the invention.
Figure 2:
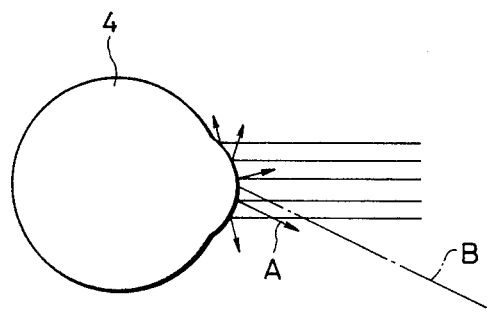
FIG. 2 is an explanatory diagram showing light beams reflected from the cornea.

A preferred embodiment of the invention will be described with reference to the accompanying drawings. FIG. 1 shows the fundamental arrangement of an eye measuring device in which the invention is used to advantage. In FIG. 1, reference numeral 1 designates an examination device having a light source 2 for applying optical energy to the eye 4 and an illuminating optical system 3. The examination device 1 is so positioned that light beams reflected from the front portion of the eye 4 are focused on the light receiving surface (not shown) of an image pickup element or a televison camera 6 is connected to a high brightness level detecting circuit 7. The detecting circuit 7 detects the presence or absence of a high brightness level during each frame scanning operation of a video signal outputted by the television camera 6. The detecting circuit 7 outputs a signal representative of the presence or absence of the high brightness level during a period commencing at the completion of one frame scanning operation and ending at the completion of the next frame scanning operation.

The eye 4 is illuminated through the illuminating optical system 3 by the light source 2. As the corneal surface of the eye is spherical, the light beam illuminating the eye is regularly reflected from the cornea surface, advancing in the direction B of the optical axis of the television camera 6. The reflected light beam A has a high intensity appearing as a high brightness signal level a' in the output video signal of the television camera 6. Even if the direction of illumination or the position of the television camera is somewhat changed, a reflected high intensity light beam A is readily obtained and can be positively detected. However, in the case of such a change in direction of illumination the reflected light beam A is obtained from a different position on the cornea surface. On the other hand, the skin surface of the eyelid is a relatively excellent diffusion surface. Accordingly, as the direction of illumination is moved away from the optical axis of the eye a larger part of the illuminating light is irregularly reflected by the eyelid which, unlike the cornea surface, provides no high-intensity reflection light beam. Thus, it can be understood that when the person blinks and the eyelids are shut, the high brightness signal level a' disappears from the video signal a. The video signal a is applied to the high brightness level detecting circuit 7, one example of which is shown in block diagram form in FIG. 4. In the detecting circuit 7, the presence or absence of the high brightness signal level a' in the video signal a is detected thereby to determine whether or not the person has blinked.

Figure 4:
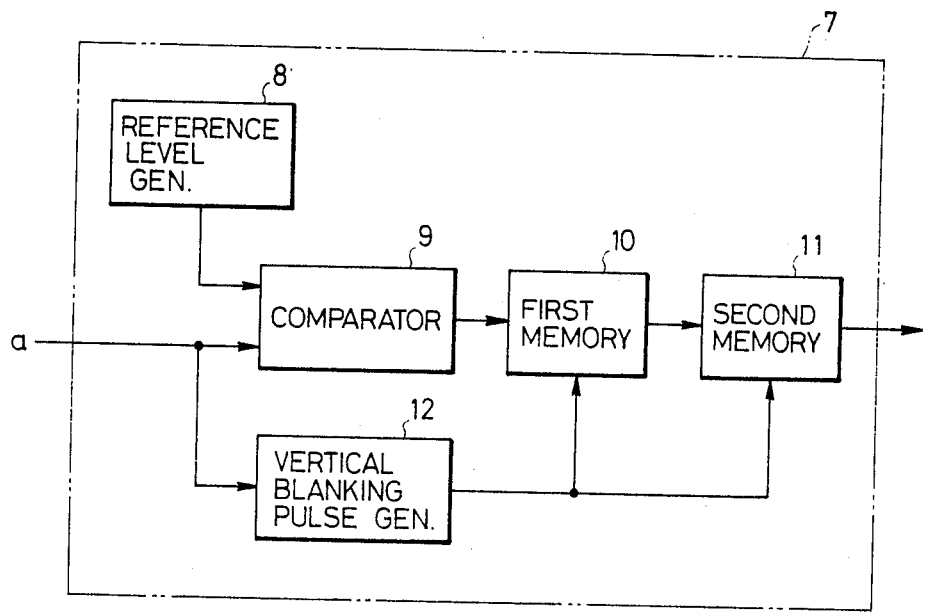
FIG. 4 is a block diagram showing one example of the detecting circuit.

Referring to FIG. 4, the video signal a is applied to one input of a comparison circuit 9 and a vertical blanking pulse generating circuit 12. The output of a reference level generating circuit 8 is applied to the other input of the comparison circuit 9. The output of the comparison circuit 9 is applied to a first memory circuit 10, the output of which is applied to a second memory circuit 11. The output of the vertical blanking pulse generating circuit 12 is supplied to the first and second memory circuits 10 and 11.

Figure 3:
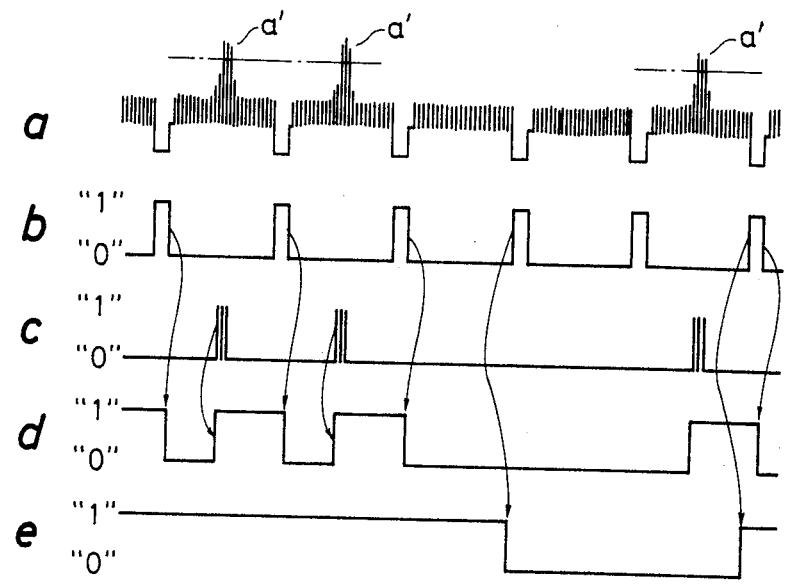
FIG. 3 is a time chart for a description of the operations of signals in a detecting circuit shown in FIG. 4.

The reference level generating circuit 8 produces a threshold level which is slightly lower than the high-intensity signal level a'. The threshold level is compared with the video signal a by the comparison circuit 9. When the eye is open, the video signal a includes the high intensity signal level a' as was described before and therefore the video signal exceeds the threshold level provided by the reference level generating circuit 8. Accordingly, during this time the comparison circuit 9 outputs a high brightness level pulse c as shown in FIG. 3. The vertical blanking pulse generating circuit 12 detects the vertical blanking component of the video signal a, to generate a vertical blanking pulse as indicated b in FIG. 3. When the high brightness level pulse c is applied to the first memory circuit 10, the output d of the circuit 10 is raised to a logical level "1" and is maintained at "1" until the vertical blanking pulse b falls. The output "1" of the first memory circuit 10 is read by the second memory circuit 11 with the timing of rise of the vertical blanking pulse b as a result of which the output e of the second memory circuit 11 is raised to "1", thus indicating the fact that the eye is open. That is, an open-eye signal is outputted.

The first memory circuit 10 is reset by the fall of the vertical blanking pulse b, i.e. the output of the first memory circuit 10 is set to a logical level "0" so that the first memory circuit monitors when a high brightness level pulse c is outputted during the next frame scanning period.

When the person whose eyes are being examined blinks, closing the eyelids, the high brightness level a' disappears from the video signal a. Therefore, no high brightness level pulse c is outputted by the comparison circuit 9, the output of the first memory circuit 10 is maintained at "0", and the output "0" is loaded into the second memory circuit 11 with the timing of rise of the vertical blanking pulse b. As a result, the output e of the second memory circuit 11 is set to "0" thus indicating the fact that the eye has been closed. That is, a closed-eye signal is outputted. This closed-eye signal is maintained outputted while the eye is closed. When the eye is opened, the high-intensity reflected light beam from the corneal surface is detected so that the open-eye signal is outputted. Thus, the fact that the person has blinked has been detected.

As is apparent from the above description, in accordance with the invention, the reflected light beams from the retina which are affected by variations of the pupil diameter of the eye to be examined are not eliminated and the presence or absence of the desired light beam regularly reflected from the cornea is detected. Accordingly, the invention is advantageous in that measurements can be positively carried out without errors due to blinking.

With the signals representing whether the person has blinked or not, which are detected as described above, monitored by the control section of an opthalmological instrument, suitable procedures can be employed so that if the person blinks, measurement is stopped until after the blinking has ceased. Thus, the invention greatly contributes to the improvement of the reliability of the measurement.

Most of the opthalmological instruments for examining the eye with optical energy applied to the eye are provided with a television camera and a television monitor for observing the image of the eye in order to accurately position the eye to be examined and the eye examining instrument's optical system. The invention can be most suitably applied to such an instrument merely by adding the high brightness level detecting circuit shown in FIG. 4.

What is claimed is:

1. An opthalmological instrument in which optical energy is applied through a first optical system to an eye under examination and light beams reflected from the eye and analyzed to determine conditions of the eye including a blinking detecting device comprising:
   a second optical system for receiving light beams reflected from a front portion of an eye under examination to form an image of said front portion of the eye;
   image detection means disposed at an image forming plane of said second optical system; and
   detecting circuit means connected to said image detection means for determining whether a video signal produced by said image detection means falls below a predetermined threshold value and producing a digital signal indicative that blinking of the eye under examination has occurred,
   wherein said image detection means comprises a television camera, said detecting circuit means comprises a comparator, said video signal being coupled to one input of said comparator; a reference level generator having an output coupled to a second input of said comparator; a first memory having an input coupled to an output of said comparator; second memory means having an input coupled to an output of said first memory means and producing said digital signal; and vertical blanking pulse generator means having an input coupled to receive said video signal and detect a vertical blanking component thereof and an output coupled to clock inputs of said first and second memory means as a function of said vertical blanking component of said video signal.

* * * * *